United States Patent [19]

Ligtenberg et al.

[11] Patent Number: 4,701,253
[45] Date of Patent: Oct. 20, 1987

[54] ISFET-BASED MEASURING DEVICE AND METHOD FOR CORRECTING DRIFT

[75] Inventors: Hendrikus C. G. Ligtenberg, Nietap; Jozef G. M. Leuveld, Leek, both of Netherlands

[73] Assignee: Sentron v.o.f., Netherlands

[21] Appl. No.: 665,808

[22] Filed: Oct. 29, 1984

[51] Int. Cl.[4] .......................................... G01N 27/46
[52] U.S. Cl. ................................. 204/416; 204/402; 204/406; 204/433; 357/25
[58] Field of Search ............... 204/401, 402, 416, 418, 204/419, 403, 406, 408, 433; 357/25

[56] References Cited

U.S. PATENT DOCUMENTS

| | | | |
|---|---|---|---|
| 4,020,830 | 5/1977 | Johnson et al. | 204/403 |
| 4,207,146 | 6/1980 | Kunke | 204/406 |
| 4,218,746 | 8/1980 | Koshiishi | 364/571 |
| 4,269,684 | 5/1981 | Zick | 204/406 |
| 4,273,636 | 6/1981 | Shimada et al. | 204/195 P |
| 4,384,925 | 5/1983 | Stetter et al. | 204/406 |
| 4,411,741 | 10/1983 | Janata | 204/406 |
| 4,481,804 | 11/1984 | Eberhard | 204/406 |
| 4,488,556 | 12/1984 | Ho | 204/406 |
| 4,499,423 | 2/1985 | Matthiessen | 204/406 |

Primary Examiner—T. Tung
Attorney, Agent, or Firm—Henry W. Collins; Thomas R. Vigil

[57] ABSTRACT

The measuring device (10) comprises an ISFET (12) used as a chemically selective ion sensor, a reference electrode (20) positioned adjacent the ISFET (12), an amplifier (22) coupled to the ISFET and control/correction circuitry (30) coupled to the ISFET (12), to the reference electrode (20) and to the amplifier (22). The control/correction circuitry (30) is operable to maintain the drain-source current $I_{DS}$ of the ISFET (12) at a constant value and to correct drift effects of the ISFET (12) on the basis of the logarithmic equation:

$$\Delta V_p = A \ln(t/t_0 + 1)$$

where:
$\Delta V_p$ = potential drift
$A$ = scale factor for drift and amplitude
$t_0$ = time constant defining the dependence on time
$t$ = time during which the sensor is operative in the event of continuous operation.

14 Claims, 4 Drawing Figures

ISFET-BASED MEASURING DEVICE AND METHOD FOR CORRECTING DRIFT

BACKGROUND OF THE INVENTION

1. Field of the Invention

The present invention relates to a measuring device comprising an ISFET used as a chemically selective ion sensor, a reference electrode, an amplifier and a control/correction circuit. The device is operable to maintain the drain-source current $I_{DS}$ of the ISFET at a constant value.

2. Description of the Prior Art

It is known that drift effects in ISFET sensors, such as $Si_3N_4$ and $Al_2O_3$ gate ISFET sensors, are highly detrimental to the accuracy and stability of measuring systems including such ISFET sensors. These drift effects restrict the applicability of such ISFET sensors, especially in the medical field.

A further drawback inherent in ISFET sensors is the long period of adjustment required when commencing a measuring procedure. As a result of such long period, acceptably stable measurements can only be performed after this period has elapsed.

The degree of accuracy required for a biomedical pH-sensor is very high and should be at least 0.03 pH within a measuring period of a number of hours, and such accuracy preferably should be attained at the beginning of the measuring period. Many present-day ISFET sensors fail to fully meet these requirements as to accuracy.

For example, an ISFET sensor having a pH membrane/gate made of $Al_2O_3$ or $Si_3N_4$ appears to have a drift of approximately 0.02–0.06 pH/hour, and the initial drift is still far higher and may even reach values of 0.1–0.2 pH/hour during the first hour of operation of the ISFET sensor. Accordingly, such presently available ISFET sensors are not suitable for use in the biomedical field.

As will be described in greater detail hereinafter the measuring device of the present invention provides a solution to the problems of drift described above.

SUMMARY OF THE INVENTION

According to the invention there is provided a measuring device comprising an ISFET used as a chemically selective ion sensor, a reference electrode positioned adjacent said ISFET, an amplifier coupled to said ISFET, control circuit means including a clock signal generator coupled to said ISFET, to said reference electrode and to said amplifier: (a) for timing with clock signals, time periods of operation of the device; (b) for maintaining certain operating parameters of said ISFET constant while adjusting others including: $V_{DS}$ constant, $I_{DS}$ constant, $V_{RS}$, adjusted; and $V_{RS}$ constant, $I_{DS}$ constant, $V_{DS}$ adjusted; and (c) for effecting correction of drift, due to drift effects of said ISFET including adjusting the voltage supplied to said reference electrode relative to the change in potential drift, $\Delta V_p$, on the basis of the logarithmic equation:

$$\Delta V_p = A \ln (t/t_o + 1)$$

where:
$V_p$ = potential drift
$A$ = scale factor for drift and amplitude
$t_o$ = time constant defining the dependence on time
$t$ = time during which the sensor is operative in the event of continuous operation.

Further according to the invention there is provided a method for correcting drift effects of an ISFET in a measuring device comprising an ISFET used as a chemically selective ion sensor, a reference electrode, an amplifier and control circuit means including a clock signal generator for timing with clock signals, time periods of operation of the device and for maintaining certain operating parameters of said ISFET constant while adjusting others including: $V_{DS}$ constant, $I_{DS}$ constant, $V_{RS}$ adjusted; and $V_{RS}$ constant, $I_{DS}$ constant, $V_{DS}$ adjusted; said method including the step of: effecting drift correction, due to drift effects of the ISFET including adjusting the voltage supplied to the reference electrode relative to the change in potential drift, $\Delta V_p$, on the basis of the logarithmic equation:

$$\Delta V_p = A \ln (t/t_o + 1)$$

where:
$V_p$ = potential drift
$A$ = scale factor for drift and amplitude
$t_o$ = time constant defining the dependence on time
$t$ = time during which the sensor is operative in the event of continuous operation.

Still further according to the invention there is provided an ISFET suitable for use as a chemically selective ion sensor in the device as defined above which ISFET includes an ISFET chip, a protective electrode mounted on said ISFET chip adjacent an ISFET gate region, said electrode being electrically connected to the source or the bulk of said ISFET during storage; and said electrode being made of a material which has a minimal potential difference with respect to said reference electrode.

Additionally, according to the present invention there is provided a method for fabricating an ISFET having an electrode mounted on an ISFET chip adjacent an ISFET gate region, said method comprising the steps of: mounting a protective electrode on an ISFET chip adjacent an ISFET gate region, said electrode being made of a material having minimum potential difference relative to a reference electrode; electrically connecting the electrode to a source or the bulk of the ISFET so that a high DC impedance is formed in the operative range of the ISFET during operation thereof; and establishing a locally controlled electrolytic contact between the elctrode and the ISFET gate region.

DESCRIPTION OF THE PREFERRED EMBODIMENTS

Experiments with $Al_2O_3$ pH ISFET membranes or gate regions have shown that the drift effects and instability of an ISFET used as a chemically selection ion sensor are caused by a reversible bulk polarization of the $Al_2O_3$ gate region. This bulk polarization process is induced by the manner in which present-day ISFETs are operated, which operation is based on the use of direct current in a measuring device including the ISFET and by changes in the electrochemical interaction of an electrolyte and the ISFET membrane or gate region. Changes in the electrochemical interaction of an electrolyte and the ISFET membrane or gate region can be compensated for by adjusting the potential of the reference electrode by means of a feedback circuit so that the drain-source current remains constant according to the teachings of the present invention.

As a result, the reference-source potential and the drain-source potential will be continuously changing. Furthermore, all solid state drift-effects which are induced by the voltage applied, such as dielectric membrane polarization, ion movements in the dielectric etc., will tend to cause instability of a measuring device including an ISFET during the entire period of operation of the measuring device with the varying potentials $V_{DS}$ and $V_{RS}$.

The contribution of bulk polarization to drift in an ISFET sensor having an $Al_2O_3$ membrane or gate region can be defined by the following logarithmic equation:

$$\Delta V_p = A \ln (t/t_o + 1)$$

where:
$\Delta V_p$ = potential drift
A = scale factor for drift and amplitude
$t_o$ = time constant defining the dependence on time
t = time during which the sensor is operative in event of continuous operation.

Figure 1:
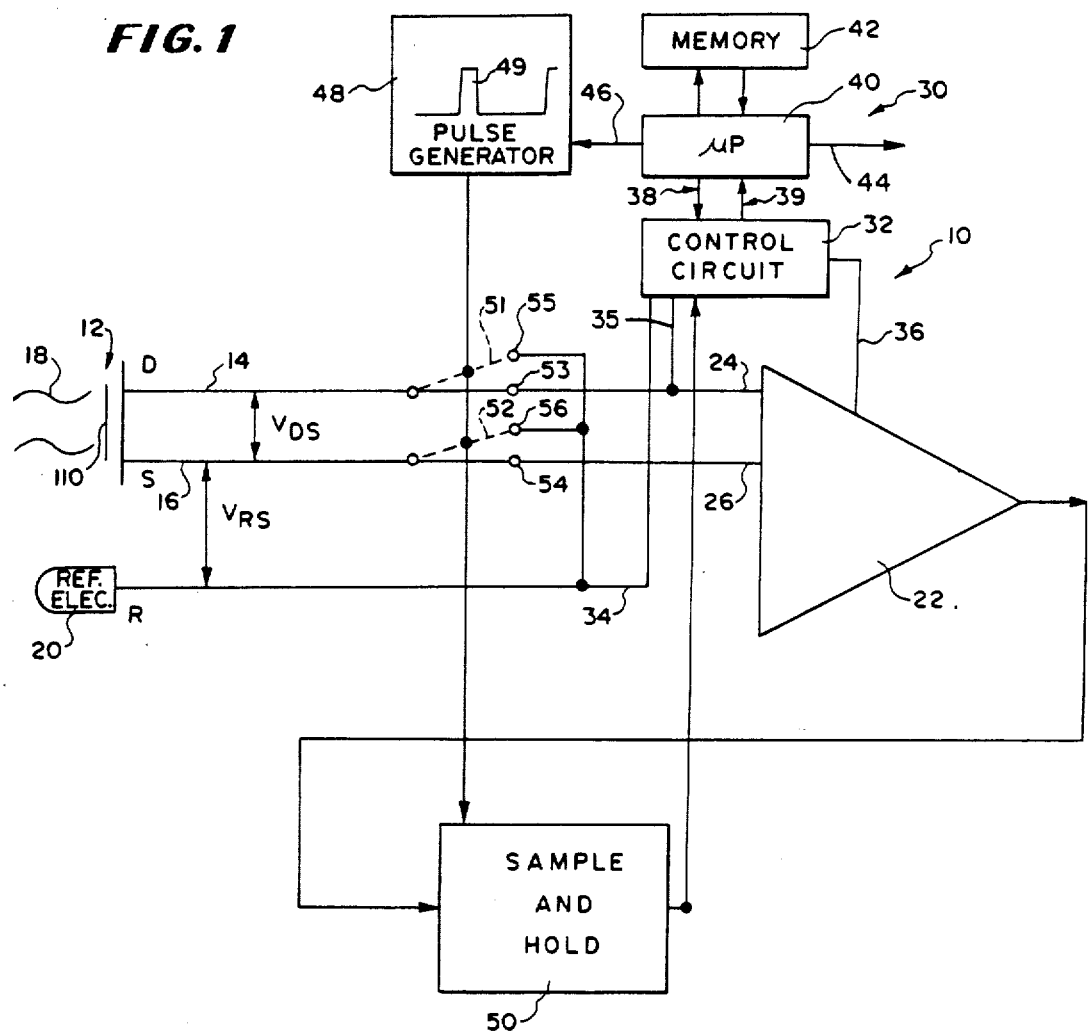
FIG. 1 is a schematic circuit diagram of the measuring device of the present invention including circuitry for supplying pulsed excitation to an ISFET of the device.

A device constructed according to the teachings of the present invention is illustrated in FIG. 1 and is generally identified by reference numeral 10. This device 10 was derived from empirical tests and includes circuitry which corrects for drift effects on the basis of the logarithmic equation:

$$\Delta V_p = A \ln (t//t_o + 1)$$

as defined above.

Also, as will be described in greater detail hereinafter, it is desirable to minimize the working duty cycle of the device 10 to minimize the drift effect, which is related to time of operation of the device 10 by operating the device 10 intermittently.

For this purpose, and as will be described below, the device 10 includes circuitry for intermittently energizing an ISFET 12 of the measuring device 10 so that its actual operating time is substantially reduced.

As shown in FIG. 1, the measuring device 10 includes the ISFET 12 which has a drain 14 and a source 16. Positioned adjacent the ISFET 12 in an electrolyte 18 is a reference electrode 20 which establishes a reference-source voltage $V_{RS}$.

As shown, the device 10 further includes an amplifier 22 having inputs 24 and 26 coupled respectively to the drain 14 and source 16 of the ISFET 12.

The device 10 further includes drift correction circuitry 30 which includes a control circuit 32 that supplies a voltage to the reference electrode 20 via a conductor 34, and supplies a voltage to the drain D of the ISFET 12 via a conductor 35, an output 36 for controlling the gain of the amplifier 22, and input-output lines or ports 38 and 39 which are coupled to a microprocessor 40.

The microprocessor 40 has a memory component 42 coupled thereto, an output 44 to which a measurement signal is supplied and a duty cycle output 46 which is connected to a pulse generator 48.

The pulse generator 48 is operable to supply a pulse 49 having a predetermined duty cycle to a sample and hold circuit 50 which, when it receives the pulse 49, samples and holds the output from the amplifier 22; and the held output is supplied via a conductor to the control circuit 32.

At the same time the pulse 49 is supplied to two switching circuits 51 and 52 shown diagramatically in FIG. 1. When the pulse 49 is received by the switching circuits 51 and 52, the switching contacts thereof are moved to positions making contact with contacts 53 and 54 connected to the drain 14 and source 16 respectively. Then, when the pulse 49 terminates for the remainder of the duty cycle, the switches 51 and 52 are caused to make connection with contacts 55 and 56 which are connected to a conductor 58 connected to the conductor 34 leading to the reference electrode 20 so as to short circuit the drain 14 and source 16 with the reference electrode 20 to render the ISFET 12 inoperable during the "OFF" portion of the duty cycle.

Figure 2:
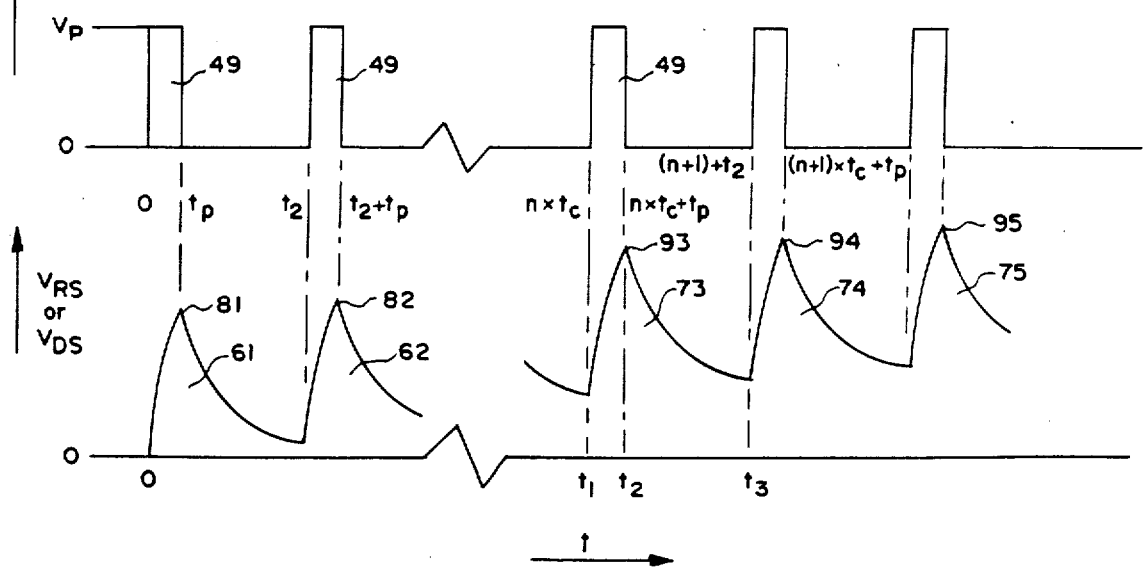
FIG. 2 is a graph of the pulsed voltage excitation versus time positioned over a graph of the ISFET voltage responding to the pulsed excitation voltage versus time.

In FIG. 2 is shown a graph of the voltage of the pulses 49 versus time superimposed over a graph of the reference-source voltage $V_{RS}$ versus time. Here it will be seen that in the pulses 61, 62 ... 73, 74, 75 ... of $V_{RS}$ there is an increasing DC offset which is the drift effect described above. In other words, the peak 82 of the pulse 62 is greater than the peak 81 of the pulse 61. Likewise, the peak 95 of the pulse 75 is greater than the peak 94 of the pulse 74 which in turn is greater than the peak 93 of the pulse 73.

In accordance with the teachings of the present invention, the correction circuitry 30 connected to and forming part of the measuring device 10 includes the memory component 42 in which the logarithmic equation:

$$\Delta V_p = A \ln (t/t_o + 1)$$

and specific values of A and t are stored so that drift effects can be corrected by the microprocessor 40 utilizing the logarithmic equation.

In this way, the device 10 can compensate for voltage drifts of $V_{DS}$ or $V_{RS}$ over relatively short measuring periods. In such instances of short measuring periods following by a long period of stabilization, high accuracy is obtained.

The correction circuit 30 of the device 10 is operable (a) to time with clock signals of the microprocessor 40 time periods of operation of the device 10; (b) to maintain certain operating parameters of the ISFET 12 constant while adjusting others including: $V_{DS}$ constant, $I_{DS}$ constant, $V_{RS}$ adjusted; and $V_{RS}$ constant, $I_{DS}$ constant, $V_{DS}$ adjusted; and (c) to effect correction of drift due to drift effects of said ISFET, including adjusting the voltage supplied to the reference electrode 20 or to the drain D of the ISFET 12 relative to changes in the potential drift, ΔVp on the basis of the logarithmic equation:

$$\Delta V_p = A \ln (t/t_o + 1)$$

where:

$V_p$ = potential drift
$A$ = scale factor for drift and amplitude
$t_o$ = time constant defining the dependence on time
$t$ = time during which the sensor is operative in the event of continuous operation.

The device 10 can also be operated over a long measuring period with less high accuracy and with a linear correction of drift being effected by the control circuit 32 based upon a first approximation utilizing the logarithmic equation defined above.

Figure 3:
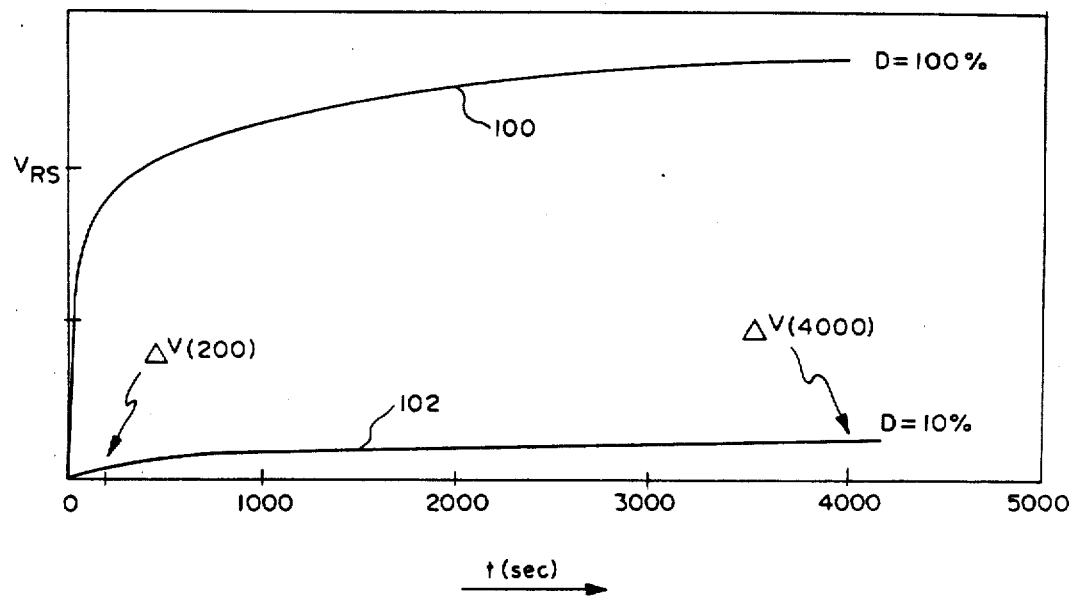
FIG. 3 is a graph of the ISFET voltage $V_{RS}$ versus time and shows the drift versus time for continuous operation and the drift for intermittent operation of a MOSFET (which is substantially equivalent to an ISFET having an $Al_2O_3$ gate region) where $V_{DS}$ and $I_{DS}$ are kept constant during the active periods.

Without knowing or determining the values of A and of t, linear correction of the voltage drift can be effected with the control circuit 32 in the measuring device 10 by first determining from a graph representing the relationship between time and drift of the voltage $V_{DS}$ or $V_{RS}$ as shown in FIG. 3. As shown in FIG. 3, the drift for 100% duty cycle is represented by a curve 100 and the drift for a duty cycle of 10% is represented by the graph 102. In this graph the abscissa is time in seconds and the ordinate is voltage, $V_{DS}$ or $V_{RS}$, in millivolts.

The graph 100 or the graph 102 is utilized to find drift values pertaining to, for example, $t_1 = 1$ hour and $t_2 = 4$ hours of operation of the device 10 after the initial actuation of the device 10. The two points found, a and b, are then interconnected by a straight line and the slope of this line is entered into the memory component 42 of the correction circuitry 30. Then, during use of the device 10 in actual practice, a correction for drift for measurements performed between one hour and four hours after actuation of the device 10 and during the time of operation of the device 10 will take place automatically on the basis of the slope stored in the memory component 42. It will be appreciated that other approximations than the linear approximation may be applied to correct the drift effects by the microprocessor 40 utilizing the logarithmic equation.

It will be appreciated that optimal elimination of the drift effect, i.e. of the DC offset shown in FIG. 2 of the responding voltage $V_{RS}$ or $V_{DS}$, is preferred. Accordingly, in a preferred embodiment of the device 10, the pulse generator 48 is provided, by which pulse excitation of the reference-source potential $V_{RS}$ and the drain-source potential $V_{DS}$ is obtained.

Changes in voltage occurring as a result of a voltage applied across ISFET membrane or gate region 110, such as the bulk polarization phenomenon which occurs in $Al_2O_3$ gate membrane material as described above, can be minimized by intermittently actuating the voltages respectively of the reference electrode 20 and across the drain-source terminals 14 and 16 with the period of actuation being very small over the duty cycle for the actuation pulses 49.

With this preferred embodiment of the device 10, as shown in FIG. 1, the ISFET sensor 12 will exhibit drift only during the periods when the ISFET sensor 12 is energized. Then, during the "OFF" period of the duty cycle, when the measuring device is de-energized, the ISFET sensor 12 recovers from the drift effect caused by the voltages imposed thereon. In this way, the drift can be reduced by a factor that, broadly speaking, is equal to the percentage of the pulse 49 over the duty cycle of the pulses 49 and will be less than when the applied voltages $V_{DS}$ and $V_{RS}$ are maintained continuously.

Intermittent operation of the device 10 is desirable also from the point of view of the practical use of the device 10. In this respect, for most uses of the measuring device 10 involving a pH-measurement, a pH-sampling rate (duration of pulse 49) of 1 second will suffice.

It has been observed that electrical charging of the surface of a dry gate insulating material can easily occur during the fabrication of an ISFET 12. The resultant potential will cause polarization of the gate material, e.g. gate region 110, to an extent at which equilibrium with the prevailing electrostatic potential is reached. As a result, during storage of an ISFET sensor 12, a potential may be present continuously across the ISFET sensor 12. When such an ISFET sensor 12 is then used in a measuring device 10 and is exposed to an electrolyte 18 into which the ISFET sensor 12 and reference electrode 20 are immersed, once the measuring device 10 is energized, the ISFET gate region 110 will tend to establish a new equilibrium with the then prevailing potential, $V_{RS}$ established by the reference electrode potential and a small contribution of the pH of the electrolyte 18.

It is to be expected that, if the reference electrode potential and the static potential during storage are substantial (for example, in excess of 0.1 volts), this potential will result in drift anomalies and non-reproducible drift phenomena.

It is therefore essential that the potential at the surface of the ISFET gate region or membrane 110 during storage is at the same potential of the reference electrode so as to provide optimal interaction of the gate region 110 with the reference electrode 20 when a measurement is made utilizing the ISFET sensor 12.

Figure 4:
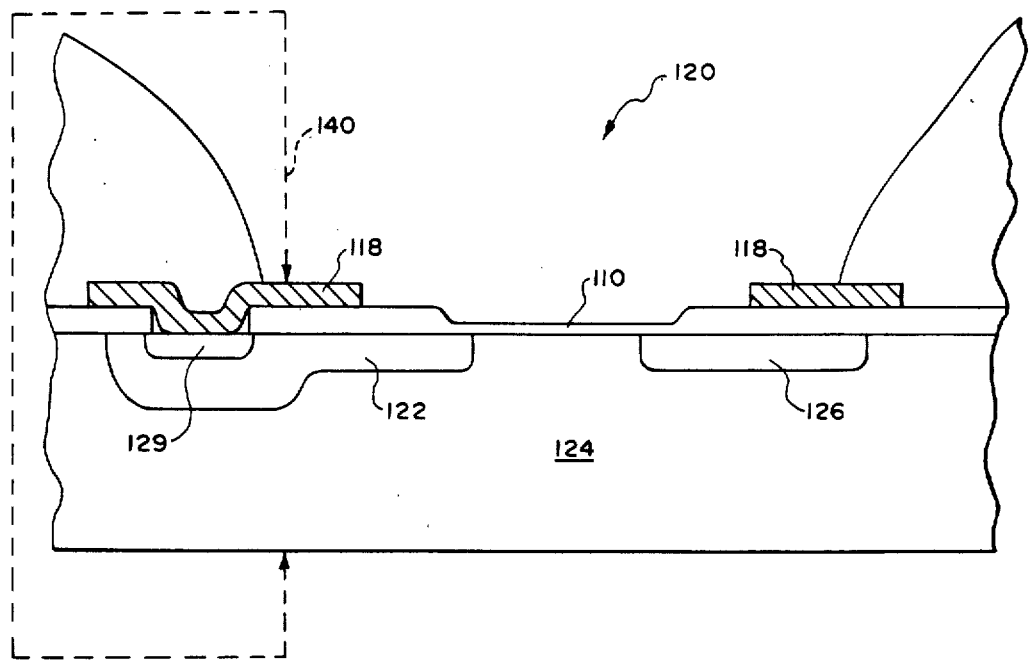
FIG. 4 is an enlarged vertical sectional view through an ISFET chip constructed according to the teachings of the present invention with portions broken away and shows a protective electrode provided adjacent a gate region of the ISFET.

To eliminate such drift anomalies, an ISFET sensor 12 suitable for use in the measuring device 10 is constructed, according to the teachings of the present invention, with a protective electrode 118 on an ISFET chip 12 as shown in FIG. 4.

As shown in FIG. 4, the electrode 118 is mounted on the ISFET chip 120 adjacent ISFET gate region 110. The electrode 118 is electrically connected to a source 122 or the bulk 124 of the chip 120. The bulk 124 is made of a p⁻ Silicon material. The source 122 is made of a n⁺ material as is a drain 126. Preferably the electrode 118 is connected through a Zener diode or avalanche diode 129 to the source 122.

In any event, the connection between the electrode 118 and the source 122 or bulk 124 has a high DC impedance in the operative range of the ISFET sensor 12 during normal operation thereof. For this purpose, the protective electrode 118 is made of a material whereby the potential difference between the protective electrode 118 and the reference electrode 20 is minimal.

By providing the connection between the protective electrode 118 and the source 122 or the bulk 124 with a high DC impedance, the electrode 118 is prevented from interferring with the behavior of the ISFET sensor 12 on the ISFET chip 120 during the contemplated use thereof.

This result is achieved by including the Zener diode or avalanche diode 129 in the electrical connection as shown in FIG. 4.

Then, during storage of the ISFET 12 the protective electrode 118 may be directly short-circuited to the source 122 or bulk 124 by means of an external connection 140 to prevent electrical charging of the gate region 110.

Although the ISFET sensor 12 and ISFET chip 120 have been described with reference to experiments made with an $Al_2O_3$ gate region for the ISFET sensor 12, the device 10 is not limited to this type of ISFET sensor 12 but can be utilized in all instances where the drift phenomenon of a solid-state electronic device induced by DC voltage is incurred.

In order to have optimal correspondence between the voltage potential at the surface of the ISFET gate material 110 during storage and the reference electrode 20 during measurements by the measuring device 10, the manufacture of the ISFET sensor 12 comprises the additional step of mounting the electrode 118 on the ISFET chip 120 adjacent the ISFET gate region 110. Such electrode 118 is made of a material providing a minimal potential difference relative to the reference electrode 20. Also, the protective electrode 118 is electrically connected to the source 122 or the bulk 124 in such a manner that a high DC impedance is provided in the operative range of the ISFET sensor 12 during operation thereof. Further, a locally controlled electrolytic contact between the protective electrode 118 and the ISFET gate region 110 is provided.

The EMF of various protective electrode 118 materials relative to the reference electrode 20 of the Ag/AgCl type shows that a preferred material for the protective electrode 118 is gold or silver, and preferably silver in view of its correspondence with the reference electrode 20.

The potential difference between several electrode 118 materials and an Ag/AgCl reference electrode 20 as measured in a solution of electrolytes that is comparable to blood is shown in the following table. The EMF measurements were made at room temperature.

TABLE

| Electrode 118 material | EMF generated relative to reference electrode 20 of the Ag/AgCl type |
| --- | --- |
| Aluminum (Al) | 750 mvolts |
| Gold (Au) | 60 mvolts |
| Titanium (Ti) | 670 mvolts |
| Silver (Ag) | 100 mvolts |

From the above measurements or tests, it is apparent that aluminum is not a good material for the protective electrode 118 in combination with an Ag/AgCl reference electrode 20. Such tests show that silver is a better material and is preferred for use with an Ag/AgCl reference electrode 20.

According to the teachings of the present invention, the electrolytic contact between the protective electrode 118 and the gate region 110 can be controlled by contaminating the ISFET gate region 110 with a hygroscopic salt compound, particularly NaCl, such as by immersion of the ISFET sensor 12 into an NaCl solution.

Another way of controlling the electrolytic contact is by coating the protective electrode 118 and the ISFET gate region 110 with a hydrogel such as agar-agar. It is noted that the coating of an ISFET gate region has been proposed in European published Patent Application No: 0 036 171 by Bergveld and Koning for: ELECTROCHEMICAL SENSING APPARATUS WITH IN SITU CALIBRATION AND METHOD OF MAKING SAME. Also, the coating of a catheter-tip ISFET with hydrogel is disclosed in the article entitled: "Application of catheter-tip i.s.f.e.t. for continuous in vivo measurement" by Shimada, Yano and Shibatani which appeared in Volume 18, Issue No. of the journal MEDICAL & BIOLOGICAL ENGINEERING & COMPUTING published in 1980.

From the foregoing description, it will be apparent that the measuring device 10 of the present invention, the method of using same, the ISFET sensor 12 forming a part of the measuring device 10 and the method for making the ISFET sensor 12 used in the device 10 provide a number of advantages some of which have been described above and others of which are inherent in the invention.

Also, modifications can be made to the device 10 and the ISFET sensor 12 without departing from the teachings of the present invention. Accordingly, the scope of the invention is only to be limited as necessitated by the accompanying claims.

We claim:

1. A measuring device comprising an ISFET having a drain and a source used as a chemically selective ion sensor, a reference electrode positioned adjacent said ISFET, an amplifier coupled to said ISFET, control circuit means including a clock signal generator coupled to said ISFET, to said reference electrode and to said amplifier: (a) for timing, with clock signals, time periods of operation of the device; (b) for maintaining two of the three operating parameters of said ISFET constant while adjusting the third parameter, the parameters being $V_{DS}$, $I_{DS}$ and $V_{RS}$, said controlling of the three parameters including: $V_{DS}$ constant, $I_{DS}$ constant, $V_{RS}$ adjusted; and $V_{RS}$ constant, $I_{DS}$ constant, $V_{DS}$ adjusted; and (c) for effecting correction of drift, due to drift effects of said ISFET including adjusting the voltage supplied to the reference electrode relative to changes in potential drift, $V_p$, on the basis of the logarithmic equation:

$$\Delta V_p = A \ln (t/t_o + 1)$$

where:

$\Delta V_p$ = potential drift
A = scale factor for drift and amplitude
$t_o$ = time constant defining the dependence on time
t = time during which the sensor is operative in the event of continuous operation.

2. The device of claim 1 wherein said control circuit means includes a memory component, said memory component being adapted to store the slope of a straight line drawn through a first point and a second point on an experimentally determined curve representing the drift of the device in relation to time, the first point corresponding to a point in time $t_a$ trailing the instant of initial actuation of the device and the second point corresponding to a point in time $t_b$, where $t_b > t_a$, and the measurements to be performed in the interval between $t_a$ and $t_b$ being automatically correctable on the basis of said slope.

3. The device of claim 2, wherein the point of time $t_b$ trails the instant of initial actuation of the device by four hours.

4. The device of claim 1 wherein said control circuit means includes a memory component, said logarithmic equation being stored in said memory component together with values of A and $t_o$, and said control circuit being operable to correct drift effects on the basis of said stored logarithmic equation and values of A and $t_o$.

5. The device of claim 1, including means for causing the pulsed excitation of a reference-source potential $V_{RS}$ of said ISFET and of a drain-source potential $V_{DS}$ of said ISFET.

6. The device according to claim 1, wherein said ion sensor is a plurality of ISFET sensors which can be successively actuated.

7. The device of claim 1 including an ISFET chip, a protective electrode mounted on said ISFET chip adjacent an ISFET gate region, said protective electrode being electrically connected to the source or the bulk of said ISFET during storage; and said protective electrode being made of a material which has a minimal potential difference with respect to said reference electrode.

8. The device according to claim 7, including means for directly short-circuiting said protective electrode to said source or bulk during storage of said ISFET.

9. The device according to claim 7, wherein said electrical connection of said protective electrode to said source or bulk includes a Zener diode or an avalanche diode.

10. A method for correcting drift effects of an ISFET in a measuring device comprising an ISFET used as a chemically selective ion sensor, a reference electrode, an amplifier and control circuit means including a clock signal generator for timing, with clock signals, time periods of operation of the device and for maintaining two of three operating parameters of said ISFET constant while adjusting the third parameter, the parameters being $V_{DS}$, $I_{DS}$ and $V_{RS}$, said controlling of the three parameters including: $V_{DS}$ constant, $I_DS$ constant, $V_{RS}$ adjusted; and $V_{RS}$ constant, $I_{DS}$ constant, $V_{DS}$ adjusted; said method including the steps of: effecting drift correction due to drift effects of said ISFET including adjusting the voltage supplied to the reference electrode relative to changes in potential drift, $V_p$, on the basis of the logarithmic equation:

$$\Delta V_p = A \ln (t/t_o + 1)$$

where:
$\Delta V_p$ = potential drift
A = scale factor for drift and amplitude
$t_o$ = time constant defining the dependence on time
t = time during which the sensor is operative in the event of continuous operation.

11. The method of claim 10 including the step of storing the slope of a straight line drawn through a first point and a second point on an experimentally determined curve representing the drift of the device in relation to time, the first point corresponding to a point in time $t_a$ trailing the instant of initial actuation of the device and the second point corresponding to a point in time $t_b$, where $t_b < t_a$; performing measurements in the interval between $t_a$ and $t_b$; and automatically correcting the drift in said interval on the basis of said slope.

12. The method of claim 10 wherein the point of time $t_b$ trails the instant of initial actuation of the device by four hours.

13. The method of claim 10, including the steps of: storing the logarithmic equation together with values of A and $t_o$; and correcting drift effects on the basis of the stored logarithmic equation and the values of A and $t_o$.

14. The method of claim 10, including the step of supplying pulsed excitation for a reference-source potential $V_{RS}$ of said ISFET and for a drain-source potential $V_{DS}$ of said ISFET.

* * * * *

UNITED STATES PATENT AND TRADEMARK OFFICE
CERTIFICATE OF CORRECTION

PATENT NO. : 4,701,253

DATED : October 20, 1987

INVENTOR(S) : Hendrikus C.G. Ligtenberg et al

It is certified that error appears in the above-identified patent and that said Letters Patent is hereby corrected as shown below:

Column 3, line 8, "selection" should be --selective--;

line 51, "$\Delta_p = A \ln (t//t_o + 1)$" should be --$\Delta_p = A \ln (t/t_o + 1)$--

Column 10, line 21, "$t_b < t_a$" should be --$t_b > t_a$--.

Signed and Sealed this

Twenty-eighth Day of June, 1988

*Attest:*

DONALD J. QUIGG

*Attesting Officer*  *Commissioner of Patents and Trademarks*